United States Patent
Al Ghatta et al.

(10) Patent No.: US 12,410,147 B2
(45) Date of Patent: Sep. 9, 2025

(54) SURFACTANTS

(71) Applicant: Imperial College Innovations Limited, London (GB)

(72) Inventors: Amir Al Ghatta, London (GB); Jason Patrick Hallett, London (GB); Raul Ignacio Aravena Contreras, London (GB)

(73) Assignee: IMPERIAL COLLEGE INNOVATIONS LIMITED, London (GB)

( * ) Notice: Subject to any disclaimer, the term of this patent is extended or adjusted under 35 U.S.C. 154(b) by 273 days.

(21) Appl. No.: 18/043,178

(22) PCT Filed: Sep. 3, 2021

(86) PCT No.: PCT/GB2021/052271
§ 371 (c)(1),
(2) Date: Feb. 27, 2023

(87) PCT Pub. No.: WO2022/049384
PCT Pub. Date: Mar. 10, 2022

(65) Prior Publication Data
US 2023/0416213 A1    Dec. 28, 2023

(30) Foreign Application Priority Data

Sep. 3, 2020 (GB) ..................... 2013860
Dec. 7, 2020 (GB) ..................... 2019232

(51) Int. Cl.
*C07D 307/12* (2006.01)
*C07D 307/64* (2006.01)

(52) U.S. Cl.
CPC ......... *C07D 307/12* (2013.01); *C07D 307/64* (2013.01)

(58) Field of Classification Search
CPC ..................... C07D 307/12; C07D 307/64
USPC ...................................... 549/497
See application file for complete search history.

(56) References Cited

U.S. PATENT DOCUMENTS

| | | | |
|---|---|---|---|
| 6,022,984 | A | 2/2000 | Urban et al. |
| 7,714,124 | B2 | 5/2010 | Scheibel et al. |
| 2007/0225191 | A1 | 9/2007 | Scheibel et al. |
| 2017/0226075 | A1 | 8/2017 | Stensrud et al. |
| 2018/0327375 | A1 | 11/2018 | Krumm et al. |

FOREIGN PATENT DOCUMENTS

| | | |
|---|---|---|
| CN | 108299354 A | 7/2018 |
| CN | 108299356 A | 7/2018 |
| CN | 108602791 A | 9/2018 |
| EP | 3560916 A1 | 10/2019 |
| WO | 2010033447 A2 | 3/2010 |
| WO | 2014099438 A2 | 6/2014 |
| WO | 2017079719 A1 | 5/2017 |
| WO | 2020229158 A1 | 11/2020 |

OTHER PUBLICATIONS

Chun et al., Transition-Metal-Free Poly(thiazolium) Iodide/1,8-Diazabicyclo[5.4.0]undec-7-ene/Phenazine-Catalyzed Esterification of Aldehydes with Alcohols, Organic Letters, 2017, 19(14), 3787-3790 (Year: 2017).*
Escobar et al., Biomass valorization derivatives: Clean esterification of 2-furoic acid using tungstophosphoric acid/zirconia composites as recyclable catalyst, Process Safety and Environmental Protection, 2015, 98, 176-186 (Year: 2015).*
Banerjee et al., "Carbon Dioxide Utilization via Carbonate—Promoted C—H Carboxylation", Nature Letters, vol. 531, 19 pages. Mar. 10, 2016.
Ma et al., "Cu(II)-Catalyzed Esterification Reaction via Aerobic Oxidative Cleavage of C(CO)—C(alkyl) Bonds", Chem Communication, vol. 52, pp. 2145-2148. 2016.
Zhang et al., "Automation of Fluorous Solid-Phase Extraction for Parallel Synthesis", J. Comb. Chem., vol. 8, pp. 890-896. 2006.
Combined Search and Examination Report in GB Application No. 2013860.8, 6 pages. Feb. 10, 2021.
Gassama et al., "Sulfonated Surfactants Obtained from Furfural", Green Chemistry, vol. 15, pp. 1558-1566. 2013.
International Search Report and Written Opinion in International Application No. PCT/GB2021/052271, 16 pages. Dec. 21, 2021.
Kraus et al., "A Direct Synthesis of Renewable Sulfonate-Based Surfactants", J. Surfact. Deterg., vol. 16, pp. 317-320. 2013.
Luo et al., "Direct Alkoxycarbonylation of Heteroarenes via Cu-Mediated Trichloromethylation and In Situ Alcoholysis", Organic Letters, vol. 22, pp. 2093-2098. 2020.
Park et al., "Tunable Oleo-Furan Surfactants by Acylation of Renewable Furans", ACS Central Science, vol. 2, pp. 820-824. 2016.
Van Es et al., "Use of Furandicarboxylic Acid and Its Decyl Ester as Additives in the Fischer's Glycosylation of Decanol by D-Glucose: Physicochemical Properties of the Surfactant Compositions Obtained", J. Surfact Deterg, vol. 16, pp. 147-154. 2013.
Suri et al., "The Mixed Surfactant System of Linear Alkylbenzene Sulfonate and Alpha Olefin Sulfonate", JAOCS, vol. 70, No. 1, pp. 59-64. Jan. 1993.

* cited by examiner

*Primary Examiner* — Kristin A Vajda
(74) *Attorney, Agent, or Firm* — Heslin Rothenberg Farley & Mesiti P.C.

(57) ABSTRACT

The present invention relates to compounds derivable from the esterification of a fatty alcohol and furoic acid according to Formula (I). The present invention also relates to the use of said compounds as surfactants, compositions comprising said compounds, and the manufacture of said compounds.

17 Claims, 3 Drawing Sheets

SURFACTANTS

CROSS REFERENCE TO RELATED APPLICATIONS

This application is a U.S. National Phase filing under 35 U.S.C. § 371 of International Application PCT/GB2021/052271, filed Sep. 3, 2021, and published as WO2022/049384A1 on Mar. 10, 2022. PCT/GB2021/052271 claims priority from Great Britain application number 2013860.8, filed Sep. 3, 2020 and Great Britain application number 2019232.4, filed Dec. 7, 2020. The entire contents of each of these prior applications are hereby incorporated herein by reference.

FIELD OF INVENTION

This invention relates to compounds that can function as surfactants, their use in detergents and the manufacture of said compounds.

BACKGROUND

Surfactants are one of the most used chemical commodities, commercialized in high volumes and finding application in many different fields, for example in household, industrial, agriculture and personal care products. Due to the high volumes in which they are produced, sustainability in terms of feedstock used, synthesis procedure, biodegradability and formulations are important parameters to assess the success of a surfactant.

Surfactant design is based on the selection of the chemical structure of the hydrophilic and hydrophobic parts of a surfactant compound. Evaluation of a surfactant can be accomplished by evaluating different parameters such as critical micelle concentration (CMC), Krafft temperature (KP), resistance to hard water, foaming, solubility, emulsifying proprieties, toxicity and biodegradability. In order to meet a good compromise between all these parameters, many known detergents are a formulation of different chemical compounds where the surfactant is the active ingredient, making up between 15 to 40% of the formulation, with additives such as builders, chelants and hydrotropes included to optimise the performance of the surfactant.

Linear alkyl benzene sulfonate (LAS) has been extensively used as a surfactant in detergent applications, as described in Suri, S. K.; Thakur, M. S.; Bhardwaj, S.; J. Am. Oil Chem. Soc. 1993, 70 (1), 59-64. https://doi.org/10.1007/BF02545368. However, additives need to be blended with LAS to obtain detergent formulations with suitable detergent properties. Some of the additives that must be present to tune the properties of LAS are believed to harm the environment. For example, sodium tripolyphosphate (STPP), ethylenediaminetetraacetate (EDTA), and sodium nitrilotriacetate, which are used to increase the hard water resistance of LAS, are considered toxic to human and/or aquatic life. Other more environmentally friendly builders, such as zeolites or citric acid, are currently used, but these additives are more expensive and/or more difficult to formulate into detergents.

In addition, LAS is made from non-renewable, petroleum-based feedstocks. For this reason, bioderived sodium dodecyl sulfate (SDS), which can be produced from renewable sources such as palm kernet, coconut oil or fatty acids, has been used as an alternative to LAS.

However, SDS has limited utility because it performs poorly in hard water, exhibits a high CMC, and like LAS, must be formulated with additives that can be expensive and/or harmful to the environment to improve its performance.

Alternative surfactants have been proposed in Gassama et al, Green Chem, 2013, 15, 1558-1566, Kraus & ee, J. Surfact. Deterg. (2013) 16: 317-320, US20170226075 and US20180327375.

It remains desirable to provide new surfactants with improved properties, such as: being derivable from biorenewable and/or low cost feedstocks; good performance in hard water; high solubility; and/or low CMC. It is also desirable that the new surfactants can be formulated into detergents while using fewer builders, chelants and hydrotropes.

SUMMARY OF THE INVENTION

This disclosure relates to a new class of surfactants derived from the esterification of a fatty alcohol and furoic acid.

In a first aspect of the invention, there is provided a compound of Formula (I):

wherein $R_1$ is

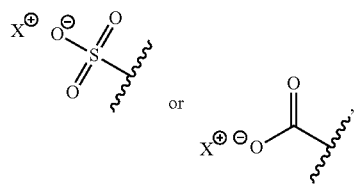

wherein X is a cation; and $R_2$ is an acyclic $C_8$ to $C_{18}$ aliphatic group.

A second aspect of the invention relates to the use of a compound of Formula (I) as a surfactant.

In a third aspect, the invention provides a composition comprising a compound of Formula (I), wherein the composition is a detergent composition, a personal care composition, an oil recovery composition, a pharmaceutical composition, an agricultural composition or a paint composition.

In a fourth aspect, the invention provides a process for manufacturing a compound of Formula (Ia):

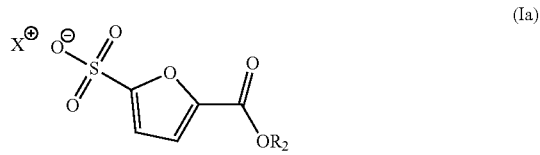

comprising the steps of:
a) contacting a compound of Formula (II):

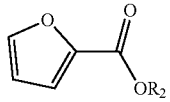 (II)

with a sulfonation agent; and
b) adding a base to form the compound of Formula (Ia); wherein X and $R_2$ are as defined in the first aspect of the invention.

In a fifth aspect, the invention provides a process for manufacturing a compound of Formula (Ib):

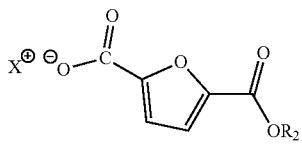 (Ib)

comprising the steps of:
a) contacting a compound of Formula (II):

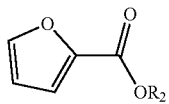 (II)

with a carboxylation agent; and
b) adding an acid to form the compound of Formula (Ib); wherein X and $R_2$ are as defined in the first aspect of the invention.

In a sixth aspect, the invention provides a composition comprising a compound of Formula (I) and sodium dodecyl sulfate.

In a seventh aspect, the invention provides a compound of Formula (II) wherein $R_2$ is as defined in the first aspect of the invention.

In an eighth aspect, the invention provides process for manufacturing a compound of Formula (II):

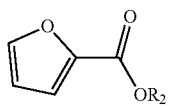 (II)

comprising the step of contacting furoic acid with a compound of Formula (III):

$R_2$—OH (III)

wherein $R_2$ is as defined in the first aspect of the invention; optionally in the presence of an acid.

In a ninth aspect, the invention provides a process for manufacturing a compound of Formula (II):

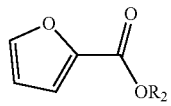 (II)

comprising the step of contacting furfural with a compound of Formula (III):

$R_2$—OH (III)

wherein $R_2$ is as defined in the first aspect of the invention; in the presence a source of oxygen and a catalyst.

DETAILED DESCRIPTION

Figure 1:
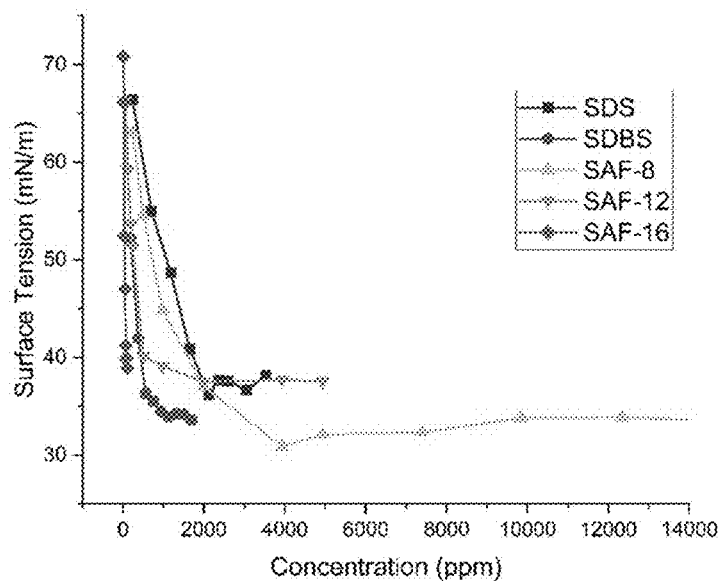
FIG. 1—Measurement of surface tension at different concentration—shows the change in surface tension of an aqueous solution of different surfactant as a function of surfactant concentration.

In a first aspect of the invention, there is provided a compound of Formula (I):

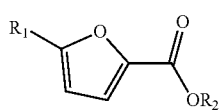 (I)

wherein $R_1$ is

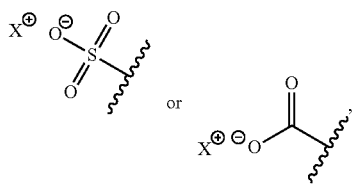

wherein X is a cation; and $R_2$ is an acyclic $C_8$ to $C_{18}$ aliphatic group.

For compounds of Formula (I), X is a cation. X may be an alkali metal cation, an alkaline earth metal cation or an ammonium cation. X may be a sodium cation, a potassium cation, a lithium cation, a calcium cation, a magnesium cation, or an ammonium cation. X may be an alkali metal cation, for example, a sodium cation or a potassium cation.

$R_2$ is an acyclic $C_8$ to $C_{18}$ aliphatic group. $R_2$ may be a saturated acyclic $C_8$ to $C_{18}$ aliphatic group, for example, a $C_8$ to $C_{18}$ alkyl group. $R_2$ may be an unsaturated acyclic $C_8$ to $C_{18}$ aliphatic group, for example, a $C_8$ to $C_{18}$ alkene. $R_2$ may be a straight-chain $C_8$ to $C_{18}$ aliphatic group. $R_2$ may therefore be a straight-chain $C_8$ to $C_{18}$ alkyl group. $R_2$ may alternatively be a branched $C_8$ to $C_{18}$ alkyl group. $R_2$ may also be an unsaturated straight-chain $C_8$ to $C_{18}$ aliphatic group.

$R_2$ contains from eight to eighteen carbon atoms. $R_2$ may contain from eight to sixteen carbon atoms. $R_2$ may, for example, be a $C_8$ aliphatic group, a $C_{12}$ aliphatic group or a $C_{16}$ aliphatic group. Indeed, $R_2$ may be a straight-chain $C_8$ alkyl group, a straight-chain $C_{12}$ alkyl group, or a straight-chain $C_{16}$ alkyl group.

$R_1$ is either

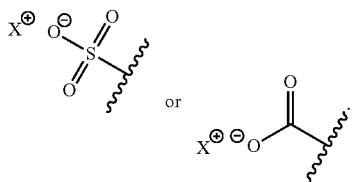

Compounds of Formula (I) therefore include compounds of Formula (Ia):

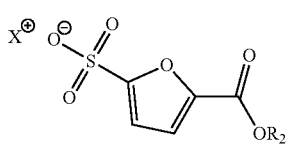

(Ia)

wherein $R_2$ is an acyclic $C_8$ to $C_{18}$ aliphatic group as described above. Compounds of Formula (I) also include compounds of Formula (Ib):

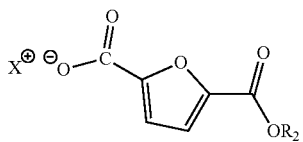

(Ib)

wherein $R_2$ is an acyclic $C_8$ to $C_{18}$ aliphatic group as described above.

Exemplary compounds of Formula (I) include:

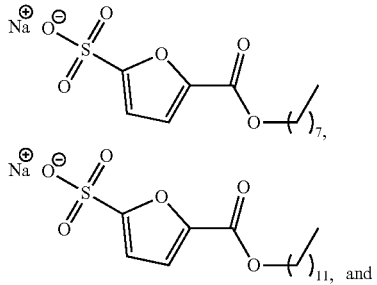

-continued

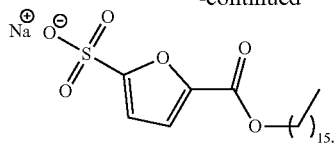

In a second aspect, the invention relates to the use of a compound of the first aspect of the invention as a surfactant. A compound of the first aspect, or a mixture of compounds of the first aspect, may be used as a surfactant. The compounds of the first aspect of the invention may be used in a detergent composition. The compounds of the first aspect of the invention may be used to remove a contaminant from a surface. Exemplary surfaces include ceramics, metals, glasses, plastics, fabrics or some combination of these.

A third aspect of the invention relates to providing a compound of the first aspect in a detergent composition. Accordingly, a detergent composition may comprise a compound, or a mixture of two or more compounds, of the first aspect. Detergent compositions may comprise a carrier and/or one or more additives, for example, the detergent composition may also comprise one or more builders, chelants, or hydrotropes, and combinations thereof. Exemplary builders include zeolites and citric acid. Exemplary chelants include sodium tripolyphosphate (STPP), ethylenediaminetetraacetate (EDTA), and sodium nitrilotriacetate. Exemplary hydrotropes include ureas, tosylates (such as the sodium salt of toluene sulfonic acid or the potassium salt of toluene sulfonic acid), cumenesulfonates (such as the sodium salt of cumene sulfonic acid or the ammonium salt of cumene sulfonic acid) and xylenesulfonates (such as the potassium salt of xylenesulfonic acid, the calcium salt of xylene sulfonic acid, or the ammonium salt of xylene sulfonic acid). A detergent composition may be free of hydrotropes. Any of these additives can be included in the final formulation to further enhance the proprieties of the detergent. In addition to their use in detergents, the compounds of the first aspect may be used as part of a personal care composition, an oil recovery composition, a pharmaceutical composition, a drug delivery composition, an agricultural composition a coating composition, or a paint composition. The compounds of the first aspect may be used in any formulation or process that requires emulsification (e.g. radical polymerization processes).

A composition comprising a mixture of two or more compounds of the first aspect may be provided.

A mixture of compounds of the first aspect, which may be provided for use as a surfactant and/or in a detergent composition, may comprise two or more compounds of the first aspect. A mixture of two or more compounds of the first aspect may also be provided in a personal care composition, an oil recovery composition, a pharmaceutical composition, a drug delivery composition, an agricultural composition a coating composition, or a paint composition. In such a mixture, the two or more compounds may have $R_2$ groups of differing chain length. The mixture may comprise a compound of the first aspect wherein $R_2$ is an acyclic $C_8$ to $C_{11}$ aliphatic and a compound of the first aspect wherein $R_2$ is an acyclic $C_{12}$ to $C_{18}$ aliphatic. For example, the mixture may comprise a compound of the first aspect wherein $R_2$ is an acyclic $C_8$ aliphatic and a compound of the first aspect wherein $R_2$ is an acyclic $C_{12}$ to $C_{18}$ aliphatic. The mixture may comprise a compound wherein $R_2$ is a straight chain or branched $C_8$ alkyl (e.g. a straight chain $C_8$ alkyl) and a compound wherein $R_2$ is a straight chain or branched $C_{12}$ to $C_{18}$ alkyl (e.g. a straight chain $C_{12}$ to $C_{18}$ alkyl). The mixture may comprise a compound wherein $R_2$ is a straight chain or branched $C_8$ alkyl (e.g. a straight chain $C_8$ alkyl) and a compound wherein $R_2$ is a straight chain or branched $C_{12}$ to $C_{18}$ alkyl (e.g. a straight chain $C_{12}$ to $C_{18}$ alkyl). The mixture may comprise a compound wherein $R_2$ is a straight chain or branched $C_8$ alkyl (e.g. a straight chain $C_8$ alkyl) and a compound wherein $R_2$ is a straight chain or branched $C_{12}$ or $C_{16}$ alkyl (e.g. a straight chain $C_{12}$ or $C_{16}$ alkyl). The mixture may comprise a compound wherein $R_2$ is a straight chain or branched $C_8$ alkyl (e.g. a straight chain $C_8$ alkyl) and a compound wherein $R_2$ is a straight chain or branched $C_{12}$ alkyl (e.g. a straight chain $C_{12}$ alkyl).

The mixture may comprise a mixture of two or more of:

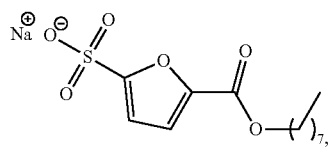,

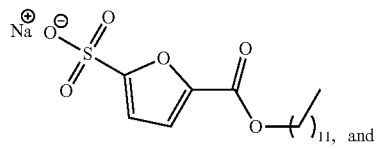, and

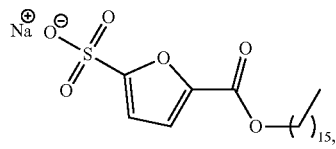

for example a mixture of

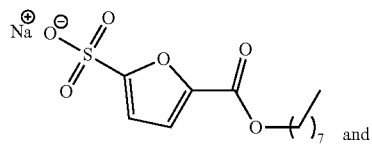 and

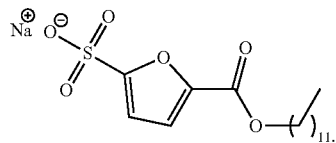.

Any of the above mixtures may comprise the two compounds at a weight ratio of about 2:1 to 1:2, for example about 1:1.

Synthesis of Compounds of Formula (I)

A compound of Formula (I) can be prepared by the following synthetic route:

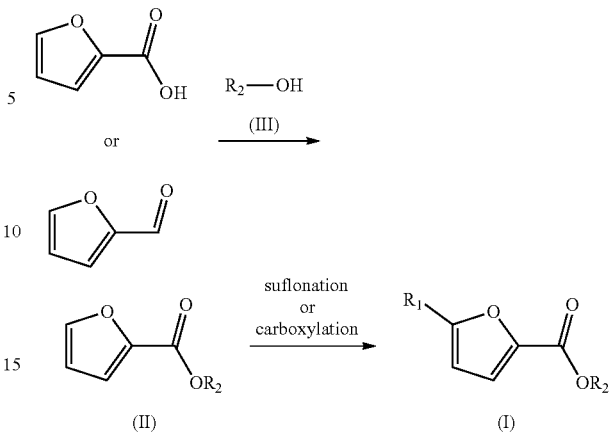

where $R_1$ and $R_2$ are as described above.

Accordingly, a fourth aspect of the invention provides a process for manufacturing a compound of Formula (Ia):

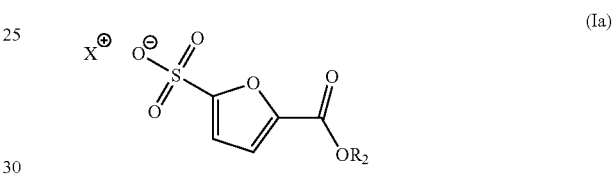

(Ia)

comprising the steps of:
a) contacting a compound of Formula (II):

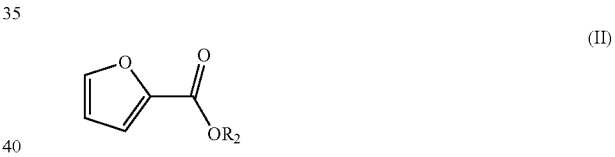

(II)

with a sulfonation agent; and
b) adding a base to form the compound of Formula (Ia); wherein X and $R_2$ are as described above.

Step a) of the process requires the compound of Formula (II) to be contacted with a sulfonation agent. The sulfonation agent may be a pyridine/sulfur trioxide complex, oleum, sulfur trioxide or chlorosulfonic acid. The sulfonation agent (for example chlorosulfonic acid) may be provided in at least a stoichiometric amount (a 1:1 molar ratio) relative to the amount of compound of Formula (II) provided. The sulfonation agent (for example chlorosulfonic acid) may be provided in excess relative to the amount of compound of Formula (II) provided. For example, the sulfonation agent (for example chlorosulfonic acid) may be provided at an equivalence of 1.05 or more relative to the amount of compound of Formula (II).

Step a) may be carried out with or without a solvent. When a solvent is used, chloroform may be used as the solvent. Liquid sulfur dioxide may also be used as a solvent, for example liquid sulfur dioxide may be used as a solvent, with solubilized sulfur trioxide as the sulfonation agent.

Step a) may be carried out at a temperature of 20° C. or greater. For example, a temperature of 60° C. or greater may be used, a temperature ranging from 60° C. to 80° C. may be used, or a temperature ranging from 60° C. to 70° C. may be used.

Step b) of the process requires the addition of a base so that the compound of Formula (Ia) is obtained as a salt, the form in which it will be provided for use as a detergent. Base may be added to achieve neutralisation, for example to reach pH 7 or higher. Suitable bases include alkali metal hydroxides or alkali metal carbonates. Suitable alkali metal hydroxides include sodium hydroxide or potassium hydroxide. Suitable alkali metal carbonates include sodium carbonate or potassium carbonate.

A fifth aspect of the invention provides a process for manufacturing a compound of Formula (Ib):

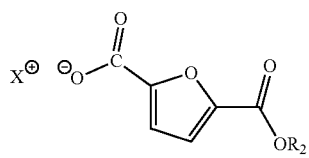

(Ib)

comprising the steps of:
a) contacting a compound of Formula (II):

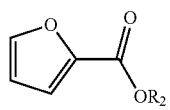

(II)

with a carboxylation agent; and
b) adding an acid to form the compound of Formula (Ib);
wherein X and $R_2$ are as described above.

Step a) of the process requires the compound of Formula (II) to be contacted with a carboxylation agent. The carboxylation agent may be carbon dioxide. This reaction can be improved by providing a mixture of i) a compound of Formula (II), ii) carbon dioxide, and iii) an alkali metal carbonate or an alkaline earth metal carbonate, or a combination thereof. For example, component iii) could be potassium carbonate or caesium carbonate or a combination thereof. Step a) may be conducted at a temperature ranging from about 200 to about 300° C. and a pressure of about 8 bar to about 40 bar.

Step b) of the process requires the addition of an acid so that that the compound of Formula (Ia) is obtained as a salt, the form in which it will be provided for use as a detergent. Acid may be added to achieve neutralisation, for example to reach pH 7 or lower.

Processes for making compounds according to Formula (Ia) or Formula (Ib) can also include the step of first preparing a compound of Formula (II). This can be achieved by forming an ester between a fatty alcohol and a furan derivative. For example, a compound of Formula (II) can be prepared by contacting furoic acid with a compound of Formula (III):

$R_2$—OH  (III)

wherein $R_2$ is an acyclic $C_8$ to $C_{18}$ aliphatic group as defined above; optionally in the presence of an acid as catalyst.

This reaction may be carried out using an excess of furoic acid relative to the amount of compound of Formula (III) provided. For example, where furoic acid may be provided at an equivalence of 1.2 or more relative to the amount of compound of Formula (III). Alternatively, the reaction may be carried out using an excess of compound of Formula (III) relative to the amount of furoic acid provided.

The process may be carried out in the presence of an acid catalyst. The acid catalyst may be a Lewis acid or a Brønsted acid. The acid may be provided in an amount of from 0.1 to 10.0 mol %, for example 0.1 to 5.0 mol %, 0.1 to 2.0 mol %, 0.1 to 1.0 mol %, or 1.0 to 2.0 mol % relative to the amount of compound of Formula (III) provided.

The acid may be sulfuric acid, or a polymer that comprises sulfonic acid functional groups (well-known examples of which include Nafion, Aberlyst-15 or Purolite-C450). The acid may be sulfuric acid provided in an amount of from 1.0 to 2.0 mol % relative to the amount of compound of Formula (III) provided.

The process may be carried out without an acid being present. For example, the process may be carried out without a solvent and without an acid at a temperature of 160° C. or greater.

The reaction may be carried out with or without a solvent. When the reaction is carried out without a solvent, the reaction may be carried out at a temperature high enough to solubilise the compound of Formula (III) in the furoic acid provided. For example, a temperature of 120° C. or greater may be used, or a temperature of 140° C. or greater may be used, or a temperature ranging from 140° C. to 160° C. may be used. When the reaction is carried out with a solvent, an aprotic organic solvent may be used. When a solvent is used, the reaction may be carried out a temperature of 60° C. or greater.

An alternative way of preparing a compound of Formula (II) is to contact furfural with a compound of Formula (III):

$R_2$—OH  (III)

wherein $R_2$ is an acyclic $C_8$ to $C_{18}$ aliphatic group as defined above; in the presence a source of oxygen and a catalyst.

In this method, a suitable source of oxygen may be di-tert-butyl peroxide or hydrogen peroxide or gaseous oxygen or air. A suitable catalyst may comprise a noble metal or transition metal. The noble metal or transition metal may be zero valent, or may be part of a metal complex. Suitable noble metal or transition metal complexes include noble metal carbenes or transition metal carbenes. The noble metal or transition metal may be used as a catalyst in bulk, or supported on another substance. A suitable support may comprise carbon, titania, zeolite or zirconia. Suitable noble or transition metals include gold, palladium, platinum, ruthenium, manganese, cobalt or vanadium.

Compositions Comprising Compounds of Formula (I) and Sodium Dodecyl Sulfate (SDS)

It has been found that when a compound of Formula (I) is provided as part of a mixture with sodium dodecyl sulfate (SDS), the mixture exhibits improved solubility in water.

Accordingly, a sixth aspect of the invention provides a composition comprising a compound of Formula (I) as defined above and SDS. The composition may be provided in different ratios of the compound of Formula (I) and SDS, for example, they could be provided in a mass ratio of from about 1:6 to about 6:1 of the compound of Formula (I) and SDS respectively. The composition may comprise a compound of Formula (I) wherein $R_1$ is

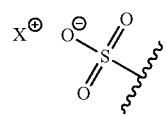

and $R_2$ is a straight chain $C_{12}$ alkyl, and SDS, wherein the mass ratio is about 6:1. The composition may comprise

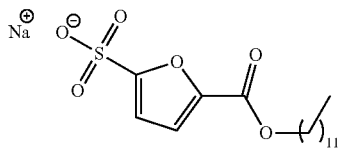

and SDS, wherein the mass ratio is about 6:1.

Compounds of Formula (II)

A seventh aspect of the invention provides compounds of Formula (II):

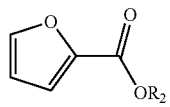

(II)

wherein $R_2$ is as defined above.

Accordingly, an eight aspect of the invention provides a process for manufacturing a compound of Formula (II):

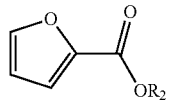

(II)

comprising the step of contacting furoic acid with a compound of Formula (III):

$R_2$—OH  (III)

wherein $R_2$ is as defined in the first aspect of the invention; optionally in the presence of an acid. The conditions that may be used to carry out this process are those described above in relation to the fourth and fifth aspects of the invention when a compound of Formula (II) is being obtained from furoic acid.

Likewise, a ninth aspect of the invention provides a process for manufacturing a compound of Formula (II):

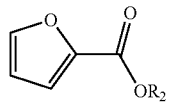

(II)

comprising the step of contacting furfural with a compound of Formula (III):

$R_2$—OH  (III)

wherein $R_2$ is as defined in the first aspect of the invention; in the presence a source of oxygen and a catalyst. The conditions that may be used to carry out this process are those described above in relation to the fourth and fifth aspects of the invention when a compound of Formula (II) is being obtained from furfural.

The term "aliphatic," as used herein, includes both saturated and unsaturated, nonaromatic, hydrocarbons which may be straight chain (i.e., unbranched), branched, acyclic, cyclic, or combinations thereof. The term "aliphatic" includes alkyl, alkenyl, alkynyl, cycloalkyl, and cycloalkenyl moieties. The term "acyclic aliphatic" as used herein includes both saturated and unsaturated hydrocarbons, which may be straight chain or branched. An unsaturated acyclic aliphatic contains one or more carbon-carbon double or triple bonds. The term "acyclic aliphatic" includes straight chain or branched alkyl (fully saturated), alkenyl (including at least one carbon-carbon double bond) or alkynyl (including at least one carbon-carbon triple bond) moieties.

The term "sulfonation agent" as used herein refers to a reagent that can be used to provide a sulfonic acid group to an organic compound. The term "carboxylation agent" as used herein refers to a reagent that can be used to provide a carboxylic acid group to an organic compound.

The term "ammonium cation" as used herein refers to an $[NH_4]^+$ cation, a primary ammonium cation ($[NH_3R]^+$), a secondary ammonium cation ($[NH_2R_2]^+$), a tertiary ammonium cation ($[NHR_3]^+$) or a quaternary ammonium cation ($[NR_4]^+$). Each R may independently be a hydrocarbon, for example, an aliphatic hydrocarbon, an aromatic hydrocarbon, or a hydrocarbon comprising both aliphatic and aromatic moieties. The aliphatic hydrocarbon may be, for example, an alkyl group. An alkyl group may, for example, be a $C_1$ to $C_{18}$ alkyl group, a $C_1$ to $C_{12}$ alkyl group, or a $C_1$ to $C_6$ alkyl group. Where R comprises an aromatic group, for example, where R is a phenyl or benzyl group, the aromatic group may optionally be substituted, for example with one or more halogens (for example a fluorine, chlorine, bromine or iodine), or one of more alkyl groups.

The term "about" is used herein to mean approximately, in the region of, roughly, or around. When the term "about" is used in conjunction with a numerical range, it modifies that range by extending to boundaries above and below the numerical range set forth. In general, the term "about" is used herein to modify a numerical value above and below the stated value by a variance of 10%.

Throughout the description and claims of this specification, the words "comprise" and "contain" and variations of the words, for example "comprising" and "comprises", mean "including but not limited to", and are not intended to (and do not) exclude other components. In any of the embodiments described herein, reference to "comprising" also encompasses "consisting essentially of" and "consisting of".

The present disclosure will now be explained in more detail by reference to the following non-limiting examples.

EXAMPLES

Abbreviations

LAS=Linear alkyl benzene sulfonate
SDS=sodium dodecyl sulfate;
SDBS=Sodium dodecylbenzenesulfonate;
SAF=sulfonated alkyl furoate Materials:

Furoic Acid (98%), 1-octanol (>99%), 1-dodecanol, 1-hexadecanol (99%), fuming sulfuric acid (20% $SO_3$), chlorosulfonic acid (99%), sulfur trioxide pyridine complex (97%), pharmaceutical grade sodium dodecylbenzenesulfonate (SDBS) and sodium dodecyl sulfate were obtained from Sigma Aldrich. Octyl furoate (>97%) was obtained by TCI. Dichloromethane (DCM), chloroform and sulfuric acid (5 M) were obtained from VWR. Chloroform was purified from ethanol by washing with water (3 times 3:1 ratio) and distilled over phosphorous pentoxide in a distillation tower. The solvent was stored in a dark container to avoid decomposition. All other chemicals were used without purification if not otherwise stated.

Example 1: Synthesis of Octyl Furoate

Octanol (100 g, 0.768 mol, 1 eq) was mixed with furoic acid (103.3 g, 0.926, 1.2 eq) in a round bottom flask followed by the addition of sulfuric acid (1 mol % respect octanol, 1.54 ml). The reaction was heated at 140° C. and left until the alcohol was completely consumed (4-5 h). The reaction mixture was diluted with DCM (200 ml) and filtered to remove byproducts and unreacted furoic acid. The organic phase was washed with water (400 ml) to remove residual acidity until neutral pH was reached. Since the emulsion could not be broken up by centrifugation, sodium chloride or ethanol had to be added during the washing to separate the phases. Solvent removal under vacuum gave the crude product (90% yield). The product was further purified by distillation under vacuum under activated charcoal.

Octyl Furoate: $^1$H NMR (DMSO-$d_6$): δ 8 (m, —C—CH—O—), 7.3, 6.7 (m×2, 2×1H, 2×C—CH—C), 4.23 (t, 2H, O—CH2—CH2, $J_{HH}$=6.6 Hz), 1.66, 1.4-1.8 (m, CH2 alkyl chain), 0.86 (m, CH$_2$—CH$_3$). $^{13}$C{$^1$H} NMR (DMSO-$d_6$): δ 159.9 (C=O), 147.8 (CH—C—C=O), 144.6 (O—CH—CH), 119, 113 (—C—CH—CH—C), 65 (O—CH2-CH2), 31.7, 31.1, 29.1, 28.7, 25.8, 22.7 (6×C, C—CH2-C), 14.4 (—CH$_2$—CH$_3$) ppm. MS (ES, -ve mode): m/z=225.1486. FT-IR: 1705 cm$^{-1}$ (O—C=O stretching).

Example 2: Synthesis of Sulfonated Octyl Furoate (SAF-8)

Octyl furoate (30 g, 0.134 mol) was added to dry chloroform (1 l) and mixed at room temperature until full dissolution had been achieved. The reaction flask was then connected to a water-filled bubbler through which the HCl produced was vented. Chlorosulfonic acid (CSA) was then added (16.6 g, 0.140 mol, 1.05 eq). The reaction was left until no bubbling was observed in bubbler and then analysed by $^1$H NMR spectroscopy to confirm that the reaction was complete with full conversion of the ester and reaction of most of the CSA (CSA shift: 10.9 ppm). Chloroform was removed under vacuum to afford a green solution which was diluted with water and neutralized to pH 7 with sodium hydroxide solution. Water was then removed under vacuum to provide the crude product as a black solid. The product needed to be purified to remove residual sodium sulfate salts (formed by neutralization of the excess of chlorosulfonic acid) as well as the impurities responsible for the dark colour by dissolution in dichloromethane and filtered followed with washing three times with diethyl (200 ml). Upon washing, the surfactant was obtained as a white powder (70% yield).

Sulfonated Octyl Furoate: $^1$H NMR (D$_2$O): 6.9, 6.7 (m×2, 2×1H, 2×C—CH—C), 4.2 (t, 2H, O—CH2—CH2, $J_{HH}$=6.6 Hz), 1.6, 1.34-1.0 (m, CH2 alkyl chain), 0.8 (m, CH$_2$—CH$_3$). $^{13}$C{$^1$H} NMR (D$_2$O): δ 158.5 (C=O), 155.8 (O—CH—CH) 144.5 (CH—C—C=O), 118.2-112.2 (—C—CH—CH—C), 66.1 (O-CH2-CH2), 31.7, 29.2, 29.1.2, 28.3, 25.7, 22.6 (6×C, C—CH2-C), 13.8 (—CH$_2$—CH$_3$) ppm. MS (ES, -ve mode): m/z (abundance)=303.087 (C$_{13}$H$_{19}$O$_6$S·100%). FT-IR: 1250-1300 cm-1, S=O stretching), 1705 cm$^{-1}$ (O—C=O stretching).

Example 3: Synthesis of Dodecyl Furoate

Dodecanol (100 g, 0.54 mol, 1 eq) was mixed with furoic acid (72.58 g, 0.648, 1.2 eq) in a round bottom flask followed by the addition of sulfuric acid (1 mol % respect dodecanol, 1.08 ml). The reaction was heated at 140° C. and left until the alcohol was completely consumed (4-5 h). The reaction mixture was diluted with DCM (200 ml) and filtered to remove byproducts and unreacted furoic acid. The organic phase was washed with water (400 ml) to remove residual acidity until neutral pH was reached. Since the emulsion could not be broken up by centrifugation, sodium chloride or ethanol had to be added during the washing to separate the phases. Solvent removal under vacuum gave the crude product (87% yield). The product was further purified by distillation under vacuum under activated charcoal.

Dodecyl Furoate: $^1$H NMR (DMSO-$d_6$): δ 7.9 (m, —C—CH—O—), 7.2, 6.7 (m×2, 2×1H, 2×C—CH—C), 4.23 (t, 2H, O—CH$_2$—CH$_2$, $J_{HH}$=6.6 Hz), 1.66, 1.4-1.8 (m, CH$_2$ alkyl chain), 0.86 (m, CH$_2$—CH$_3$). $^{13}$C{$^1$H} NMR (DMSO-$d_6$): δ 159.9 (C=O), 148.2 (CH—C—C=O), 144.5 (O—CH—CH), 119, 112.5 (—C—CH—CH—C), 65.7 (O—CH2-CH2), 31.8, 29.5, 29.2, 29.7, 28.8, 25.9, 22.6 (8×C, C—CH2-C), 14.1 (—CH$_2$—CH$_3$) ppm. MS (ES, -ve mode): m/z=281.2109. FT-IR: 1705 cm$^{-1}$ (O—C=O stretching).

Example 4: Synthesis of Sulfonated Dodecyl Furoate (SAF-12)

Dodecyl furoate (30 g, 0.107 mol) was added to dry chloroform (1 l) and mixed at room temperature until full dissolution had been achieved. The reaction flask was then connected to a water-filled bubbler through which the HCl produced was vented. Chlorosulfonic acid (CSA) was then added (13.1 g, 0.112 mol, 1.05 eq). The reaction was left until no bubbling was observed in the bubbler and then analysed by $^1$H NMR spectroscopy to confirm that the reaction was complete with full conversion of the ester and reaction of most of the CSA (CSA shift: 10.9 ppm). Chloroform was removed under vacuum to afford a green solution which was diluted with water and neutralized to pH 7 with sodium hydroxide solution. Water was then removed under vacuum to provide the crude product as a black solid. The product needed to be purified to remove residual sodium sulfate salts (formed by neutralization of the excess of chlorosulfonic acid) as well as the impurities responsible for the dark colour by dissolution in dichloromethane and filtered followed with washing three times with diethyl (200 ml). Upon washing, the surfactant was obtained as a white powder (64% yield).

Dodecyl Furoate: $^1$H NMR (DMSO-$d_6$): δ 7.9 (m, —C—CH—O—), 7.2, 6.7 (m×2, 2×1H, 2×C—CH—C), 4.23 (t, 2H, O—CH$_2$—CH$_2$, $J_{HH}$=6.6 Hz), 1.66, 1.4-1.8 (m, CH$_2$ alkyl chain), 0.86 (m, CH$_2$—CH$_3$). $^{13}$C{$^1$H} NMR (DMSO-$d_6$): δ 159.9 (C=O), 148.2 (CH—C—C=O), 144.5 (O—CH—CH), 119, 112.5 (—C—CH—CH—C), 65.7 (O—CH2-CH2), 31.8, 29.5, 29.2, 29.7, 28.8, 25.9, 22.6 (8×C, C—CH2-C), 14.1 (—CH$_2$—CH$_3$) ppm. MS (ES, -ve mode): m/z (abundance)=359.0865 (C$_{17}$H$_{27}$O$_6$S·100%). FT-IR: 1100-1300 cm-1, S=O stretching), 1705 cm$^{-1}$ (O—C=O stretching).

Example 5: Synthesis of Hexadecyl Furoate

Hexadecanol (100 g, 0.412 mol, 1 eq) was mixed with furoic acid (55.4 g, 0.495, 1.2 eq) in a round bottom flask followed by the addition of sulfuric acid (1 mol % respect hexadecanol, 0.824 ml). The reaction was heated at 140° C. and left until the alcohol was completely consumed (4-5 h). The reaction mixture was diluted with DCM (200 ml) and filtered to remove byproducts and unreacted furoic acid. The organic phase was washed with water (400 ml) to remove residual acidity until neutral pH was reached. Since the emulsion could not be broken up by centrifugation, sodium chloride or ethanol had to be added during the washing to separate the phases. The product was crystallized from DCM at −20° C. to give a white powder (89% yield).

Hexadecyl Furoate: $^1$H NMR (benzene-d$_6$): δ 7.0, 6.9 (m×2, 2×1H, 2×C—CH—C), 5.8 (m, —C—CH—O—), 4.1 (t, 2H, O—CH2—CH2, $J_{HH}$=6.7 Hz), 1.44, 1.37-1.05 (m, CH2 alkyl chain), 0.85 (m, CH$_2$—CH$_3$). $^{13}$C{$^1$H} NMR (benzene-d6): δ 158.5 (C=O), 145.7 (CH—C—C=O), 145.5 (O—CH—CH), 117, 111 (—C—CH—CH—C), 64.4 (O—CH2-CH2), 32, 29.9-29.3, 28.8, 26, 23 (6×C, C—CH2-C), 14.1 (—CH$_2$—CH$_3$) ppm. MS (ES, −ve mode): m/z=337.2735. FT-IR: 1705 cm$^{-1}$ (O—C=O stretching).

Example 6: Synthesis of Sulfonated Hexadecyl Furoate (SAF-16)

Hexadecyl furoate (30 g, 0.0892 mol) was added to dry chloroform (1 l) and mixed at room temperature until full dissolution had been achieved. The reaction flask was then connected to a water-filled bubbler through which the HCl produced was vented. Chlorosulfonic acid (CSA) was then added (10.9 g, 0.09366 mol, 1.05 eq). The reaction was left until no bubbling was observed in bubbler and then analysed by $^1$H NMR spectroscopy to confirm that the reaction was complete with full conversion of the ester and reaction of most of the CSA (CSA shift: 10.9 ppm). Chloroform was removed under vacuum to afford a green solution which was diluted with water and neutralized to pH 7 with sodium hydroxide solution. Water was then removed under vacuum to provide the crude product as a black solid. The product was washed with small amounts of water to remove the sulfate salt by exploiting the low solubility of this surfactant in the water phase. THF proved to be efficient in removing the impurities, leaving the surfactant as a white powder.

Sulfonated Hexadecyl Furoate: $^1$H NMR (D$_2$O): δ 6.9, 6.7 (m×2, 2×1H, 2×C—CH—C), 4.1 (t, 2H, O—CH2-CH2, $J_{HH}$=6.4 Hz), 1.54, 1.26-0.95 (m, CH2 alkyl chain), 0.8 (m, CH$_2$—CH$_3$). $^{13}$C{$^1$H} NMR (D$_2$O): δ 159.5 (C=O), 156.5 (O—CH—CH) 144.6 (CH—C—C=O), 118.9-112.9 (—C—CH—CH—C), 66.1 (O—CH2-CH2), 32.2, 31-29.3, 28.5, 26, 22.8 (10×C, C—CH2-C), 13.8 (—CH$_2$—CH$_3$) ppm. MS (ES, −ve mode): m/z (abundance)=415.1465 (C$_{21}$H$_{36}$O$_6$S·100%). FT-IR: 1100-1300 cm-1, (S=O stretching), 1705 cm$^{-1}$ (O—C=O stretching).

Example 7: Solubility Study

The solubility studies of different surfactants were performed according to ISO standard 6839 (Determination of solubility in water). In a typical test, 20 ml of solution with a surfactant concentration between 12.5-22.5% w/w was prepared in duplicate and heated using a controlled temperature hotplate until fully dissolved. 10 ml of solution was poured into a 20 ml vial and allowed to cool until precipitation was observed. Other 10 ml of solution was poured into a 20 ml vial and kept at a higher temperature. The precipitated sample was slowly heated and the clear sample was slowly cooled. The temperature at which an appearance change occurred was considered the temperature of solubility at a specific surfactant concentration. Results of the solubility test are reported in Table 1.

TABLE 1

Result of solubility test for different surfactants concentrations as a function of temperature at which dissolution was observed.

| Concentration (% weight) | SDS (° C.) | SDBS (° C.) | SAF-8 (° C.) | SAF-12 (° C.) | SAF-16 (° C.) |
| --- | --- | --- | --- | --- | --- |
| 22.5 | >50 | >50 | <0 | <0 | >50 |
| 20 | 41-43 | >50 | <0 | 20-25 | >50 |
| 17.5 | 34-35 | — | <0 | 20-25 | >50 |
| 15 | 27-29 | 43-45 | <0 | 20-25 | >50 |
| 12.5 | 27-29 | — | <0 | 20-25 | >50 |

The commercial SDBS prove to have the lowest solubility due to the extensive hydrophobicity imparted by the benzene ring while SDS achieved higher solubility at 10-15% at room temperature. Although the solubility of SDS is higher than SDBS, SDS will still require the addition of hydrotropes to increase its solubility when used. Remarkable improvements were achieved by swapping to a furan head with an ester linkage, especially for the SAF-8 where high solubility was achieved at very low temperatures. At room temperature the SAF-8 could be solubilized at concentration up to 140%. SAF-12 was soluble at 20% at 24° C., but would precipitate at temperatures below 20° C. The effect of the alkyl chain becomes evident in SAF-16, which was found to have very low solubility. At room temperature 0.05% of SAF-16 was soluble in the water phase. The SAF-8 could be used as a detergent without adding hydrotropes, while SAF-16 may be used with a hydrotrope. SAF-12 may be used as a detergent for hot water applications alone, i.e. without a hydrotrope, or with a hydrotrope for cold water applications. Mixtures with SAF-8 can be used to improve the solubility of higher alkyl chain SAF. By means of example, a mixture of 20% SAF-8 and % SAF-12 exhibited solubility at a temperature down to 7° C.

Example 8: Resistance to Hard Water

These measurements were made according the standard protocol reported in ISO standard 1063. Calcium chloride was used as cation source at concentrations of 6, 9 and 12 m equivalent Ca/L (3.0, 4.5, 6.0 mM). A mother solution of surfactant with 50 mg/ml concentration was prepared in water at 20° C. In a 50 ml falcon-tube, a defined aliquot of mother solution was transferred and diluted up to 50 ml with the calcium solution. Five different aliquots of surfactant mother solution were tested: 5.0, 2.5, 1.2, 0.6 and 0.3 ml. In every test, the appearance of the sample was inspected and assigned a score according to Table 2. The scores of the 15 tests for each surfactant were summed and the final result was expressed as mean stability according to Table 3.

TABLE 2

Score corresponding to the appearance of the liquid.

| Appearance of the liquid | Score number |
| --- | --- |
| Clear | 5 |
| Opalescent | 4 |
| Cloudy | 3 |
| Slight precipitate | 2 |
| Heavy precipitate | 1 |

Opalescent is a solution not clear but which objects can be seen. Cloudy is a solution not clear which objects cannot be seen through.

TABLE 3

Mean stability table

| Total Score | Mean Stability |
|---|---|
| 15-18 | 1 |
| 19-37 | 2 |
| 38-56 | 3 |
| 57-74 | 4 |
| 75 | 5 |

The results of the stability tests are reported in Table 4. SDBS and SDS proved to have very low resistance to hard water and exhibited extensive precipitation in many tests. On the other hand, SAF-8 and SAF-12 showed very good solubility, and the solutions remained clear at all different calcium concentrations.

TABLE 4

Results of hard water stability test

|  | Total Score | Mean Stability |
|---|---|---|
| SDS | 21 | 2 |
| SDBS | 50 | 3 |
| SAF-8 | 75 | 5 |
| SAF-12 | 75 | 5 |
| SAF-12/SDS (6:1) | 75 | 5 |

Example 9: Critical Micelle Concentrations Air-Water-Surfactant System

The surface tension of water-surfactant solutions was evaluated at concentrations between 10 ppm and 12.500 ppm. Concentrations that were evaluated for each surfactant varied depending on the solubility of the surfactant and the surface tension reduction observed during the analysis. The experiment was performed at 25° C. Deionised water (prepared using a Milli-Q system (Merck)) was used for each experiment.

The pendant drop method was used to calculate the surface tension by using a Krüss DSA25. A drop of the solution was produced in the tip of a blunt metal needle (1.25 mm) until the drop reached its maximum size. After 10-15 seconds of equilibration, an image of the drop was captured using a digital camera. The drop was analyzed using the software Krüss EasyDrop Standard-Drop Shape Analysis (DSA1) v 1.92. The software uses the Young-Laplace equation to calculate the surface tension according to the drop deformation considering the effect of gravity and hydrostatic pressure.

Critical micellar concentration (CMC) was obtained after plotting surface tension vs surfactant concentration. The CMC is calculated as the surfactant concentration where the initial straight line intersects the plateau in the graph. CMC results are summarized in Table 5. According these results the alkyl chain have a remarkable effect of decreasing the CMC by about 5 times for every 4 carbon atoms added. A CMC of below 2000 ppm is desirable for many commercial applications. The CMC can be improved by using mixtures of surfactants with SAF-8 to have an optimum balance between CMC and solubility as reported previously.

TABLE 5

Calculated CMC for different surfactants

| Surfactant | CMC (ppm) |
|---|---|
| SDS | 2000 |
| SDBS | 593 |
| SAF-8 | 1330 |
| SAF-12 | 521 |
| SAF16 | 60 |
| SAF-8 (20%)/SAF-12 (20%) | 989 |
| SAF-12/SDS (6:1) | 330 |

Example 10: Surface Tension Measurements in Octanol-Water-Surfactant System

The drop volume method was used to calculate the surface tension in the system following the ISO standard 9101 with some modifications. In each experiment a drop of aqueous solution of surfactant was slowly formed in the tip of a needle (d=1.82 mm) submerged in octanol using a syringe connected at a Krüss DSA25 drop shape analyser instrument. The drop formation was allowed to grow as close as possible the maximum volume at which it would detach from the needle. At this point, the drop was left to stabilize for 2 minutes and then was detached from the needle by providing a small amount of additional solution. A photo of the drop leaving the needle was captured using the camera connected to the Krüss DSA25. The diameter of the drop was measured, and the surface tension was calculated using the following equation:

$$\gamma = \frac{V \Delta \rho g}{4 \pi d f}$$

Where $\gamma$ is the surface tension (mN/m), V is the drop volume (cm$^3$), $\Delta \rho$ is the difference of density between water and octanol (g/cm$^3$), g is the acceleration due to gravity (cm/s$^2$), d is the outer diameter of the needle (cm), and f is a correction factor calculated using the following equation:

$$f = \left(2\pi \left(0.1478 + 0.2789 \frac{d}{2\sqrt[3]{V}}\right) - 0.1662 \left(\frac{d}{2\sqrt[3]{V}}\right)^2\right)^{-1}$$

Figure 2:
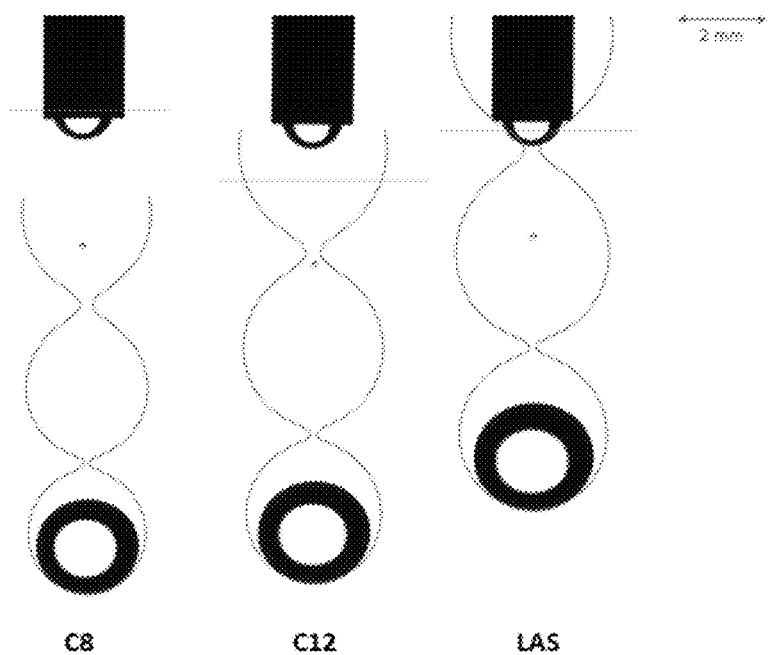
FIG. 2—Drop formation of a water/surfactant solution in octanol performed at a concentration of surfactant double of the CMC—shows an image of the droplet experiment used to measure the surface tension of surfactant solutions in octanol.

Surface tension at concentration 2 times the CMC in deionised water (prepared using a Milli-Q system (Merck)) are summarized in Table 6. It worth noticing that water in octanol exhibit a surface tension of 7.45±1.10 mN/cm, so a lower surface tension corresponds to a more favourable cleaning ability since it favours the formation of stable emulsions. In FIG. 2 the drops formation of a water/surfactant solution in octanol have been reported for the SAF-8, SAF-12 and SDBS at a concentration of surfactant double of the CMC. The SAF-8 show the lower surface tension due mostly to the high concentration of surfactant used (2.65±0.32 mN/cm). The SAF-12 show a surface tension (3.42±0.58 mN/cm) lower compared the SDBS (4.48±0.75 mN/cm) indicating that these surfactants have a high cleaning capability.

TABLE 6

Calculated surface tension for different surfactants using deionized water

| Surfactant | Surface tension (mN/cm) |
|---|---|
| SDS | 1.34 ± 0.28 |
| SDBS | 4.48 ± 0.75 |
| SAF-8 | 2.65 ± 0.32 |
| SAF-12 | 3.42 ± 0.58 |

Additionally, surface tension was evaluated using hard water (500 ppm $CaCl_2$) and results are summarized in Table 7. SAF-8 was evaluated using a concentration 2 times the CMC, while SAF-12 was evaluated at 2, 4 and 8 times the CMC. Surprisingly, SAF-8 and SAF-12 still strongly reduce the surface tension in hard water, where SDS and SDBS exhibit significant agglomeration.

TABLE 7

Calculated surface tension for different surfactants using hard water

| Surfactant | Surface tension (mN/cm) |
|---|---|
| SAF-8 | 1.91 ± 0.25 |
| SAF-12 (2 CMC) | 4.51 ± 0.50 |
| SAF-12 (4 CMC) | 3.78 ± 0.45 |
| SAF-12 (8CMC) | 1.99 ± 0.27 |

Example 11: Screening Catalysts for the Synthesis of Alkyl Furoates

To identify acid catalysts for use in converting furoic acid into alkyl furoates according to Formula (II), different catalysts were tested using the following procedure:

A stoichiometric amount of furoic acid and dodecanol (500 mg furoic acid, 830 mg dodecanol) were charged to a 3 ml vial at room temperature. A catalyst was then added to the vial (in the case of sulfuric acid, 1 mol % was added, in the case of polymeric catalysts such as Nafion or Amberlyst, 300 mg was added. The vial was placed in a preheated heating block at 150° C. for 1.5 h. The yield of dodecyl furoate and the degree of conversion of dodecanol was analysed by GC-MS-FID using naphthalene as internal standard.

Figure 3:
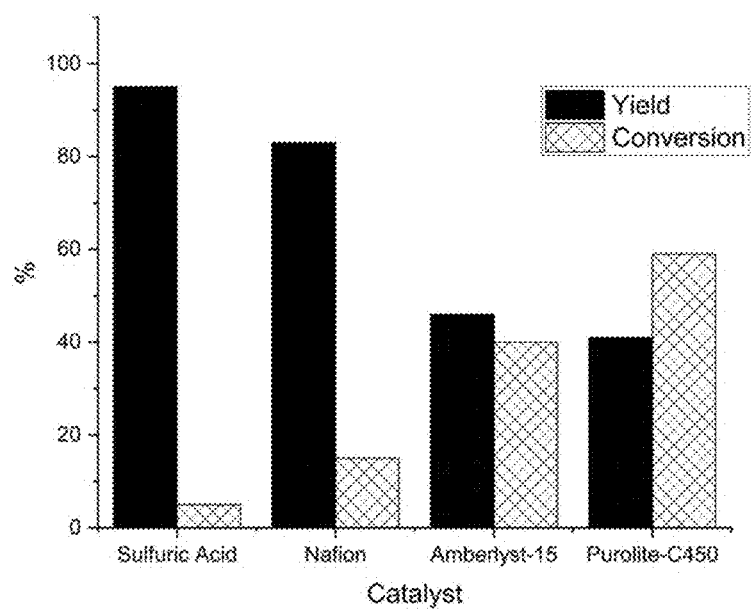
FIG. 3 shows the amount of dodecyl furoate obtained from the reaction between dodecanol and furoic acid in the presence of different catalysts.

The results of these experiments are shown in FIG. 3. The results show that each catalyst yielded dodecyl furoate. When sulfuric acid or Nafion were used, near complete conversion of starting material was observed and high yields of dodecyl furoate were obtained.

Example 12: Optimising the Amount of Catalysts to Use in the Synthesis of Alkyl Furoates To optimise the process for manufacturing alkyl furoates according to Formula (II), the conversion of furoic acid and dodecanol into dodecyl furoate was monitored in the present of different amounts of sulfuric acid catalyst.

In each experiment of furoic acid (500 mg) was mixed with a stochiometric amount of dodecanol (830 mg) and an amount of sulfuric acid (one of 0.41, 1, 1.5, 2 mol %). The reaction mixture was placed in a preheated heating block at 150° C. for 1.5 h. The yield of dodecyl furoate was analysed by GC-MS-FID using naphthalene as internal standard.

Figure 4:
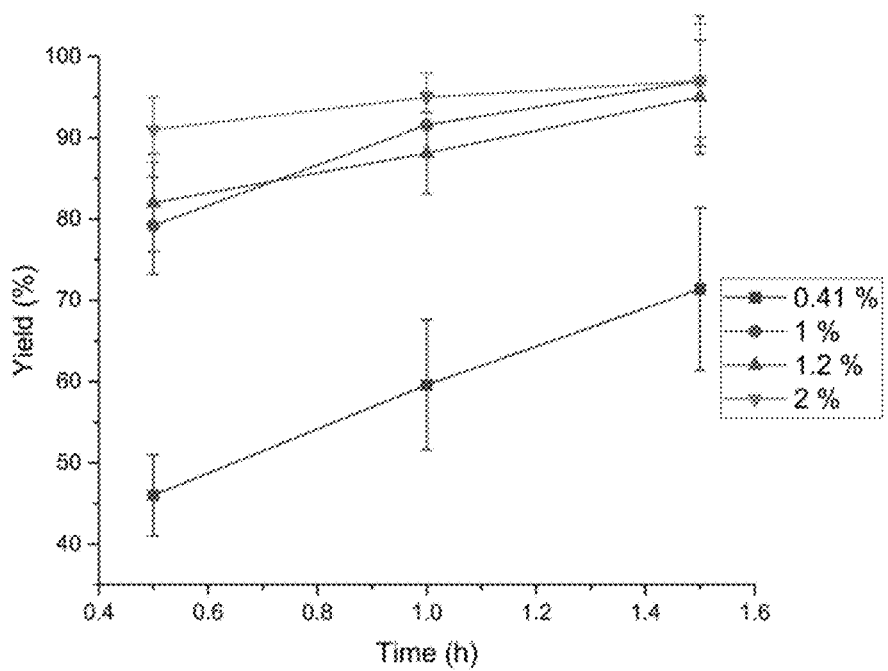
FIG. 4 shows the how the rate of production of dodecyl furoate is affected by the amount of sulfuric acid catalyst present in the reaction.

The results of these experiments are shown in FIG. 4. The results show that the reaction proceeds towards completion within 1.5 hours when 1 mol % to 2 mol % of sulfuric acid was used.

Example 13: Optimised Process for Preparing Dodecyl Furoate 1 kg of furoic acid (8.93 mol) was mixed with a stochiometric amount of dodecanol (1.66 kg) and heated until the reaction mixture reached a temperature of 150° C. 1 mol % of sulfuric acid was added. Water generated in the reaction was collected with a Dean Stark apparatus connected to a vacuum line with a pressure controller at 800 mbar. The reaction carried out for 1.5 hours. The alkyl furoate was obtained as a yellowish liquid (yield 99%). The dodecyl furoate product was confirmed by NMR and GC-MS. The residual furoic acid content was assessed to be below 2% by HPLC.

Example 14: Optimising the Reaction Temperature to Use in the Sulfonation of Alkyl Furoates To optimise the process for making surfactants according to Formula (I), the sulfonation of octyl furoate with chlorosulfonic acid was monitored while varying the reaction temperature.

In each experiment, octyl furoate (500 mg, 2.24 mmol) was mixed with a stoichiometric amount of chlorosulfonic acid (260 mg, 2.24 mmol) at room temperature and immediately placed in a preheated heating block (60, 70, 80° C.) under vigorous stirring. Samples (about 10 mg) were taken at regular intervals and diluted with water. The yield of SAF-8 was determined by HPLC using an Aminex HPX-87H column.

Figure 5:
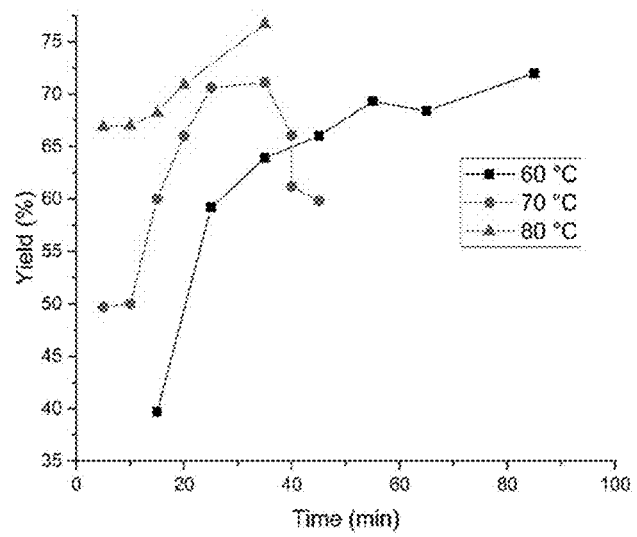
FIG. 5 shows how the rate at which octyl furoate is sulfonated by chlorosulfonic acid is affected by the reaction temperature.

The results of these experiments are shown in FIG. 5. It was found that at temperatures above 70° C., the sulfonic acid undergoes degradation when exposed to longer reaction times. An increase in yield of SAF-8 was observed at 80° C., but the mixture turned into a dark solid that would be unsuitable for use. in applications that have a specific colour specification. Sulfonation at low temperature (e.g. 70° C. or lower) leads to an optimum sulfonation yield while avoiding excessive darkening of the solution.

Example 15: Study of Foaming Capacity

Foaming capacity was evaluated following the protocol set out in ISO 6964, with some modifications. In each test, 700 mL of surfactant solution containing 0.2% surfactant was prepared using deionized water or a hard water solution of distilled water with 200 ppm of $CaCl_2$. The solutions were prepared by agitating the components for 60 minutes at 50° C. After 60 minutes, 50 mL of solution was poured in a 1000 mL glass measuring cylinder, which was then placed in a water bath that was heated to 50° C. 600 mL of the surfactant solution was poured into a chromatography column fitted with a stainless-steel needle at the egress. The column was placed over the measuring cylinder so that the tip of the needle was 450 cm from the surfactant solution in the measuring cylinder. 450 mL of surfactant solution were poured from the column into the measuring cylinder. After pouring the solution, foam height was measured at 30 sec, 3 min, 5 min and 15 min. The foam height observed after 5 minutes is reported in Table 8, below.

It was found that SDS had very good foamability in distilled water, but this decreased markedly in hard water, where it would begin to precipitate. Foam stability was improved using SAF surfactants, especially SAF-12, which achieved a greater foam height than SDS in both distilled water and hard water. This shows that the SAF surfactants are suitable for use in personal care products and can exhibit superior proprieties to SDS, even in the absence of chelants or foam boasters.

TABLE 8

Foam height recorded for the different surfactants in distilled and hard water

| Surfactant | Distilled water (mm) | Hard water (200 ppm CaCl$_2$ mm) |
| --- | --- | --- |
| SDBS | 9.25 ± 0.4 | 12.9 ± 0.1 |
| SDS | 7.25 ± 0.4 | 4.25 ± 0.4 |
| SAF 8 | 2.5 ± 0.7 | 5 ± 0.5 |
| SAF 12 | 7.8 ± 0.4 | 10.35 ± 0.5 |
| SDS/SAF-12 1:6 | 9.9 ± 0.2 | 11.12 ± 0.5 |

Example 16: Toxicity Studies

Inhibition of B-Galactosidase from *E. Coli*

The toxicity of different surfactants was analysed using a Toxi-Chromo test kit supplied by EBPI to quantify the inhibition of *E. coli* in expressing the b-galactosidase in the presence of the surfactants. Using the standard protocol, a mother solution containing 1000 ppm of a surfactant was prepared. The bacteria inoculum was mixed with a reaction mixture, nutrients supplied with the kit and the toxicant. A further 15 samples at containing different amounts of the surfactant were prepared in the well plate through subsequent dilutions. The chromogen supplied with the kit was added in each well and the well plate was then incubated at 37° C. for 30 min. The optical density (OD) was read at 600 nm using a plate reader. The % inhibition was measured by the OD variation (which is associated a blue colour development). $EC_{50}$ was measured by plotting and fitting the % inhibition and surfactant concentration.

TABLE 9

Inhibition of *E. Coli* in expressing the b-galactosidase in the present of the different surfactants

| Surfactant | $EC_{50}$ |
| --- | --- |
| SDBS | 71.9 ± 2.8 ppm |
| SDS | 123.7 ± 5.2 ppm |
| SAF 8 | 292 ± 13 ppm |
| SAF 12 | 63.5 ± 2.8 ppm |
| SDS/SAF-12 1:6 | 62.3 ± 2.5 ppm |

Inhibition of Growth of Protozoa Microorganisms

The toxicity of different surfactants was analysed using a Protoxkit supplied by microbiotests quantify the inhibition of growth of protozoa microorganisms in the presence of the surfactants. Using the standard protocol, a dilution series of toxicant was prepared by serial 1:1 dilution with distilled water. 2 mL of each solution is placed in a UV cuvette. An inoculum of Protozoa was diluted to reach an OD of 0.04 at 440 nm then 40 μL of inoculum was added along a solution of 40 μL of nutrients in each dilution vials. The initial OD was measured for each vial and the vial was then incubated at 30° C. for 24 h. Inhibition was measured by the comparing the variation of initial and final OD. $EC_{50}$ was determined as the concentration of surfactant to obtain 50% inhibition through plotting and fitting the % inhibition and surfactant concentration.

TABLE 10

Inhibition of growth of protozoa microorganisms in the presence of the different surfactants

| Surfactant | EC50 |
| --- | --- |
| SDBS | 26.9 ± 4.8 ppm |
| SDS | 85.71 ± 3.8 ppm |
| SAF 8 | 673 ± 10 ppm |
| SAF 12 | 49.65 ± 5 ppm |
| SDS/SAF 12 1:6 | 45 ± 10 ppm |

Results from the toxicity studies show that alkyl chain length has a much greater influence on toxicity than the nature of the head group. For example, SAF-8 was found to have much lower toxicity compared the other 12-carbon chain surfactants. SAF-12 was shown to have a lower toxicity than SDS, which is likely due to SAF-12 tail group having an overall longer chain (including the ester group). SAF-8 and SAF-12 both exhibited lower toxicity compared SDBS in both methodologies, which suggests that surfactants based on a furan ring head group are less toxic than those with a benzene ring head group.

Example 17: Zein Solubilisation Study

The applicability of surfactants in personal care products was studied by analysing their capacity to solubilise zein protein. In each test 2 g of zein protein was mixed with 40 ml of 0.5 wt % surfactant solution and the mixture was incubated at 40° C. for 12 h. The mixture was then centrifuged and the remaining solid zein was washed with 50 mL of water 5 times. The solid zein was dried for in an oven at 70° C. for 5 days and weighted. The zein solubilisation was evaluated as percentage of zein that was dissolved into the surfactant solution. The results in the study are shown in Table 11 below.

TABLE 11

Results of zein solubilisation study

| Surfactant | % of zein dissolved |
| --- | --- |
| SDBS | 24.6 ± 1.85% |
| SDS | 9.75 ± 0.78% |
| SAF 8 | 10.4 ± 0.98% |
| SAF 12 | 15.3 ± 0.26% |
| SDS/SAF 12 1:6 | 25 ± 0.8% |

The results of this study show that SAF-8 and SAF-12 dissolve lower amounts of zein than SDBS, and that SAF-8 performs comparably to SDS. This suggests that the new surfactants are suitable for use in personal care products and they are less irritating to the skin than commonly used surfactants such as SDBS.

Embodiments have been described by way of example and these embodiments are to be considered as illustrative and not restrictive. The present disclosure is not to be limited in terms of the particular embodiments described in this application. It will be appreciated that modifications may be made without departing from its spirit and scope, as will be apparent to those skilled in the art.

The subject matter encompassed by the following numbered embodiments also forms part of the present invention, optionally in combination with the subject matter described above and/or defined in the claims that follow.

Numbered Embodiment 1

A compound of Formula (I):

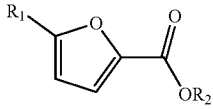
(I)

wherein $R_1$ is

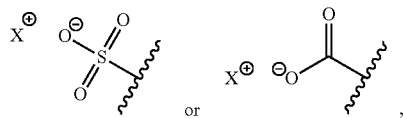

wherein X is a cation; and
$R_2$ is an acyclic $C_8$ to $C_{18}$ aliphatic group.

Numbered Embodiment 2

The compound according to Numbered Embodiment 1, wherein X is an alkali metal cation, for example a sodium cation or a potassium cation.

Numbered Embodiment 3

The compound according to Numbered Embodiment 1, wherein X is a sodium cation.

Numbered Embodiment 4

The compound according to any of Numbered Embodiments 1 to 3, wherein $R_2$ is a straight-chain $C_8$ to $C_{18}$ aliphatic group.

Numbered Embodiment 5

The compound according to Numbered Embodiment 4, wherein $R_2$ is a straight-chain $C_8$ to $C_{18}$ alkyl group.

Numbered Embodiment 6

The compound according to Numbered Embodiment 5, wherein $R_2$ is a straight-chain $C_8$, $C_{12}$ or $C_{16}$ alkyl group.

Numbered Embodiment 7

The compound according to Numbered Embodiment 4, wherein $R_2$ is an unsaturated straight-chain $C_8$ to $C_{18}$ aliphatic group.

Numbered Embodiment 8

The compound according to any of Numbered Embodiments 1 to 7, having a structure of Formula (Ia):

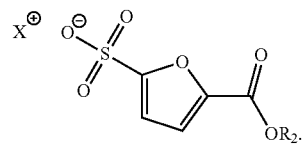
(Ia)

Numbered Embodiment 9

The compound according to any one of Numbered Embodiments 1 to 7, having a structure of Formula (Ib):

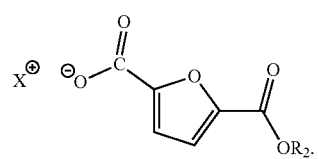
(Ib)

Numbered Embodiment 10

The compound according to any of Numbered Embodiments 1 to 8, having a structure of:

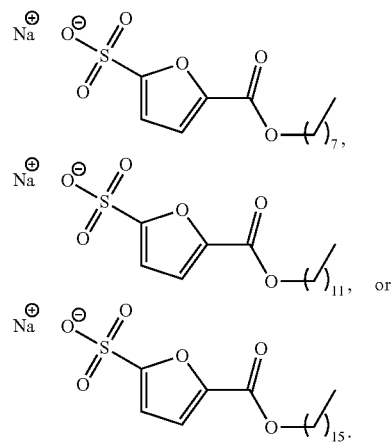

Numbered Embodiment 11

Use of a compound according to any of Numbered Embodiments 1 to 10 as a surfactant.

Numbered Embodiment 12

A detergent composition comprising a compound of any of Numbered Embodiments 1 to 10.

Numbered Embodiment 13

The detergent composition according to Numbered Embodiment 12, comprising a mixture of two or more compounds of any of claims 1 to 10.

Numbered Embodiment 14

The detergent composition accordingly to Numbered Embodiment 13, comprising a compound of any of claims 1 to 10 wherein $R_2$ is an acyclic $C_8$ aliphatic and a compound of any of claims 1 to 10 wherein $R_2$ is an acyclic $C_{12}$ or $C_{18}$ aliphatic.

Numbered Embodiment 15

A process for manufacturing a compound of Formula (Ia):

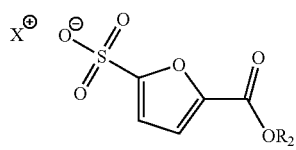
(Ia)

comprising the steps of:
contacting a compound of Formula (II):

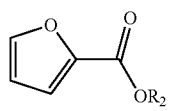
(II)

with a sulfonation agent; and
b) adding a base to form the compound of Formula (Ia), wherein X and $R_2$ are as defined in any of Numbered Embodiments 1 to 8.

Numbered Embodiment 16

The process according to Numbered Embodiment 15, wherein the sulfonation agent is selected from a pyridine/sulfur trioxide complex, oleum, sulfur trioxide or chlorosulfonic acid.

Numbered Embodiment 17

The process according to Numbered Embodiment 15, wherein the base is an alkali metal hydroxide, for example sodium hydroxide or potassium hydroxide.

Numbered Embodiment 18

A process for manufacturing a compound of Formula (Ib):

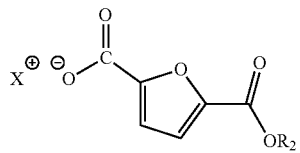
(Ib)

comprising the steps of:
contacting a compound of Formula (II):

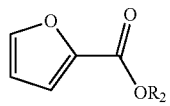
(II)

with a carboxylation agent; and
b) adding an acid to form the compound of Formula (Ib), wherein X and $R_2$ are as defined in any of Numbered Embodiments 1 to 7 and 9.

Numbered Embodiment 19

The process according to Numbered Embodiment 18, wherein the carboxylation agent is carbon dioxide.

Numbered Embodiment 20

The process according to Numbered Embodiment 19, wherein step a) comprises providing a mixture of (i) a compound of Formula (II), (ii) carbon dioxide, and (iii) an alkali metal carbonate or an alkaline earth metal carbonate, or a combination thereof.

Numbered Embodiment 21

The process according to Numbered Embodiment 19, wherein step a) comprises providing a mixture of (i) compound of Formula (II), (ii) carbon dioxide, and (iii) potassium carbonate or caesium carbonate, or a combination thereof.

Numbered Embodiment 22

The process according to any of Numbered Embodiments 18 to 21, wherein step a) is conducted at a temperature ranging from 200 to 300° C. and a pressure of 8 to 40 bar.

Numbered Embodiment 23

The process according to any of Numbered Embodiments 15 to 22, further comprising preparing a compound of Formula (II) by contacting furoic acid with a compound of Formula (III):

$R_2$—OH  (III)

wherein $R_2$ is as defined in any of Numbered Embodiments 1 and 4 to 7; in the presence of an acid.

Numbered Embodiment 24

The process according to any of Numbered Embodiments 15 to 22, further comprising preparing a compound of Formula (II) by contacting furfural with a compound of Formula (III):

$R_2$—OH  (III)

wherein $R_2$ is as defined in any of Numbered Embodiments 1 and 4 to 7; in the presence a source of oxygen and a catalyst.

Numbered Embodiment 25

The process according to Numbered Embodiment 24, wherein the source of oxygen is selected from di-tert-butyl peroxide or hydrogen peroxide.

Numbered Embodiment 26

The process according to Numbered Embodiment 24 or Numbered Embodiment 25, wherein the catalyst comprises a noble metal or a transition metal.

Numbered Embodiment 27

The process according to Numbered Embodiment 26, where said noble metal or transition metal is selected from the group consisting of gold, palladium, platinum, ruthenium, manganese cobalt or vanadium.

The invention claimed is:

1. A compound of Formula (Ia):

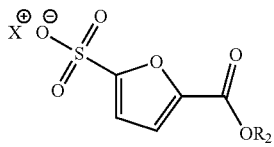

wherein X is a cation; and

R$_2$ is an acyclic C$_8$ to C$_{18}$ aliphatic group.

2. The compound according to claim 1, wherein X is an alkali metal cation.

3. The compound according to claim 1, wherein X is a sodium cation or a potassium cation.

4. The compound according to claim 1, wherein X is a sodium cation.

5. The compound according to claim 1, wherein R$_2$ is a straight-chain C$_8$ to C$_{18}$ aliphatic group.

6. The compound according to claim 5, wherein R$_2$ is a straight-chain C$_8$ to C$_{18}$ alkyl group.

7. The compound according to claim 6, wherein R$_2$ is a straight-chain C$_8$, C$_{12}$ or C$_{16}$ alkyl group.

8. The compound according to claim 5, wherein R$_2$ is an unsaturated straight-chain C$_8$ to C$_{18}$ aliphatic group.

9. The compound according to claim 1, having a structure of:

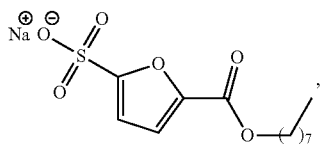

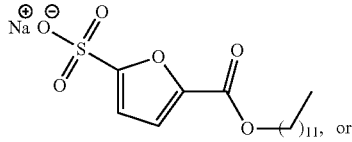

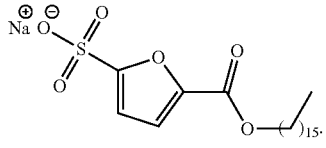

10. A surfactant, comprising a compound according to claim 1.

11. A composition comprising a compound of claim 1, wherein the composition is a detergent composition, a personal care composition, an oil recovery composition, a pharmaceutical composition, a drug delivery composition, an agricultural composition a coating composition, or a paint composition.

12. A composition comprising a mixture of two or more compounds of claim 1.

13. The composition according to claim 12, comprising a compound of claim 1 wherein R$_2$ is an acyclic C$_8$ aliphatic and a compound of claim 1 wherein R$_2$ is an acyclic C$_{12}$ or C$_{16}$ aliphatic.

14. A process for manufacturing a compound of Formula (Ia):

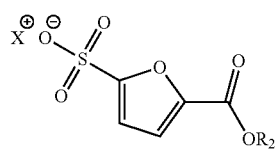

comprising the steps of:

a) contacting a compound of Formula (II):

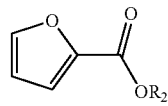

with a sulfonation agent; and b) adding a base to form the compound of Formula (Ia), wherein X and R$_2$ are as defined in claim 1.

15. A composition comprising a compound of claim 1 and sodium dodecyl sulfate.

16. The compound according to claim 1, wherein R$_2$ is a branched C$_8$ to C$_{18}$ alkyl group.

17. The compound according to claim 2, wherein the alkali metal cation is a sodium cation, a potassium cation, a lithium cation, a calcium cation, a magnesium cation, or an ammonium cation.

* * * * *